United States Patent [19]
Tam

[11] Patent Number: 4,985,178
[45] Date of Patent: Jan. 15, 1991

[54] NONLINEAR OPTICAL DEVICE FROM 3-METHYL-4-METHOXY-4'-NITROSTILBENE

[75] Inventor: Wilson Tam, Boothwyn, Pa.

[73] Assignee: E. I. du Pont de Nemours and Company, Wilmington, Del.

[21] Appl. No.: 401,871

[22] Filed: Sep. 1, 1989

Related U.S. Application Data

[63] Continuation-in-part of Ser. No. 7,275,153, Nov. 22, 1988, abandoned.

[51] Int. Cl.[5] ...................... F21V 9/04; C07C 205/00; G02B 6/10; G02B 6/00

[52] U.S. Cl. .................................... 252/587; 252/582; 568/585; 568/631; 568/630; 568/927; 568/928; 568/940; 350/96.1; 350/96.14; 350/96.12

[58] Field of Search ............... 252/582, 586, 589, 587, 252/600; 568/584, 585, 630, 631, 927, 928, 940; 350/96.1, 96.14, 96.12, 96.3

[56] References Cited

U.S. PATENT DOCUMENTS

| | | | |
|---|---|---|---|
| 3,201,481 | 8/1965 | Catino et al. | 568/631 X |
| 3,213,132 | 10/1965 | Strobel et al. | 568/631 X |
| 3,514,495 | 5/1970 | Ruby | 568/927 |
| 4,326,055 | 4/1982 | Loeliger | 568/631 X |
| 4,428,873 | 1/1984 | Murayama et al. | 252/583 |

FOREIGN PATENT DOCUMENTS

| | | | |
|---|---|---|---|
| 2204053 | 2/1988 | United Kingdom | 568/631 |

OTHER PUBLICATIONS

Franken et al., Physical Review Letters, vol. 7, 118–119 (1961).
Coda et al., J. Appl. Cryst., vol. 9, 193 (1976).
"Nonlinear Optical Properties of Organic and Polymeric Materials", D. J. Williams, ed. Am. Chem. Soc., Wash., D.C., pp. 57–80 (1983).
D. J. Williams, Angew. Chem., Int. Ed. Engl., vol. 23, 690 (1984).
"Nonlinear Optical Properties of Organic Molecules and Crystals", vol. 1, D. S. Chemla et al., Assoc. Press, Orlando, Florida, pp. 227–296 (1987).
Kurtz et al., J. Appl. Phys. 39, 3798 (1968).
Meredith et al., Macromolecules 15, 1385 (1982).
Dubois et al., Compt. Rend C284, 137, 1977.

*Primary Examiner*—Robert L. Stoll
*Assistant Examiner*—Richard Treanor

[57] ABSTRACT

A nonlinear optical element comprising 3-methyl-4-methoxy-4'-nitrostilbene useful for nonlinear optical and electro-optic effects.

8 Claims, 2 Drawing Sheets

NONLINEAR OPTICAL DEVICE FROM 3-METHYL-4-METHOXY-4'-NITROSTILBENE

RELATED APPLICATION

This application is a continuation-in-part of U.S. application Ser. No 07/275,153, filed Nov. 22, 1988, now abandoned.

BACKGROUND OF THE INVENTION

1. Field of the Invention

This invention relates to nonlinear optical systems containing 3-methyl-4-methoxy-4'-nitrostilbene, which systems are capable of second harmonic generation (SHG), electro-optic modulation, and other useful nonlinear optical and electro-optic effects 2. Description of Related Art The nonlinear optical response of a molecule can be described by the following expansion:

$$\mu=\mu_0\alpha^{(1)}E+\beta EE+\gamma EEE+\ldots$$

where $\mu$ is the induced dipole moment and $\mu_0$ is the permanent dipole moment of the molecule; $\alpha$, $\beta$, and $\gamma$ are tensors representing the linear, second order and third order polarizabilities, respectively; and E is the local electric field. The induced polarization of an ensemble of molecules, such as a crystal, can be described by the following equation:

$$P=P_0+\chi^{(1)}E+\chi^{(2)}EE+\chi^{(3)}EEE+\ldots$$

where P is the induced polarization and $P_0$ is the permanent polarization; $\chi^{(1)}$, $\chi^{(2)}$ and $\chi^{(3)}$ are tensors representing the linear, second order and third order susceptibility, respectively; and E is the applied electric field. Second order nonlinear optical phenomena such as second harmonic generation, sum and difference frequency generation, parametric processes and electro-optical effects all arise from the $\chi^{(2)}$ term.

To have a large $\chi^2$, a molecule should both possess a large $\beta$ and crystallize in a noncentrosymmetric structure. Centrosymmetric crystals have vanishing $\chi^{(2)}$ and are therefore incapable of second harmonic generation.

Franken et al., Physical Review Letters, Vol. 7 118–119 (1961), disclose the observation of second harmonic generation upon the projection of a pulsed ruby laser beam through crystalline quartz. They observed the generation of the second harmonic of light, in which light of 6943 Å was converted to light of 3472 Å. The use of a laser remains the only practical way to generate an E large enough to be able to detect the SHG phenomenon.

Coda et al., J. Appl. Cryst., Vol. 9, 193 (1976), disclose SHG in a powder sample of 4-methoxy-4'-nitrostilbene.

Useful reviews of the art relating to nonlinear properties of organic materials are given in the following references: "Nonlinear Optical Properties of Organic and Polymeric Materials", D. J. Williams, ed., American Chemical Society, Washington, D.C. pp. 57–80 (1983);

D. J. Williams, Angew. Chem., Int. Ed. Engl., Vol. 23, 690 (1984); "Nonlinear Optical Properties of Organic Molecules and Crystals", Vol. 1, D. S. Chemla, et al., ed., Associated Press, Orlando, Fla., pp. 227–296 (1987).

Ruby, U.S. Pat. No. 3,514,495, discloses a process for the preparation of 4-nitrostilbenes by the condensation of 4-nitrotoluenes with certain aromatic aldehydes. The compound which forms the basis of the present invention, 3-methyl-4-methoxy-4'-nitrostilbene, is not disclosed.

Although a large number of organic and inorganic materials capable of SHG have been found since the Franken et al. discovery, an intense search continues for new materials.

SUMMARY OF THE INVENTION

The present invention provides the novel stilbene derivative 3-methyl-4-methoxy-4'-nitrostilbene and nonlinear optical devices using a noncentrosymmetric crystalline form of this derivative.

DETAILED DESCRIPTION OF THE INVENTION

It has been found that a derivative of stilbene, 3-methyl-4-methoxy-4'-nitrostilbene (MMONS), not only has a large $\beta$, but also a large $\chi^{(2)}$. This compound has been shown to be capable of second harmonic generation, giving the largest measured value of SHG (relative to urea) of any known organic compound.

The frequency converter of the invention comprises means for producing and directing at least one incident beam of electromagnetic radiation into an optical element having nonlinear optical properties, whereby electromagnetic radiation emerging from the element contains at least one frequency different from the frequency of any incident beam of radiation, the different frequency being an even multiple of the frequency of the incident beam of electromagnetic radiation. The optical element comprises crystalline 3-methyl-4-methoxy-4'-nitrostilbene crystallized in a noncentrosymmetric space group.

Figure 1:
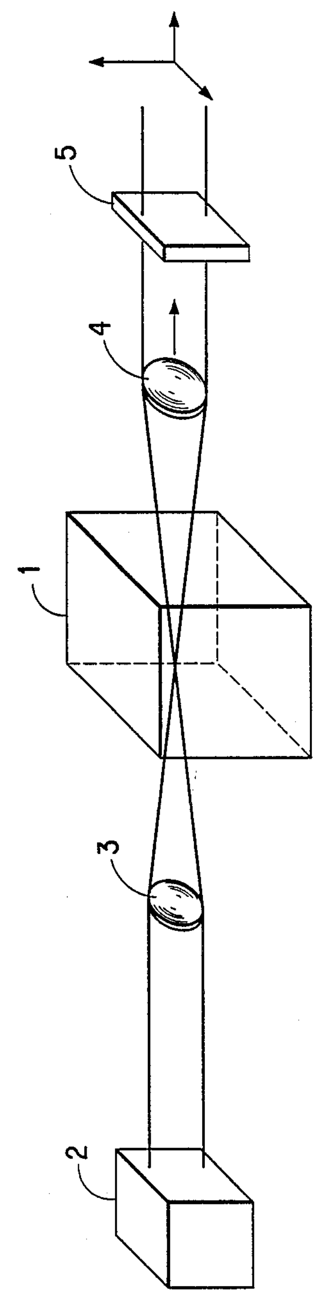
FIG. 1 is a schematic view of a frequency converter according to the invention.

Preferably, the emerging radiation of a different frequency is doubled (second order) (SHG). Preferably, the electromagnetic radiation is radiation from one of a number of common lasers, such as Nd-YAG, Raman-shifted Nd-YAG, semiconductor diode, and Ar or Kr ion Referring now to FIG. 1, optical element 1 is oriented in one of a potentially infinite number of crystal orientations which achieve partially maximized SHG conversion by virtue of phase matching The specific orientation is chosen for reasons of noncriticality, maximum nonlinearity, increased angular acceptance, etc. Polarized light of incident wavelength $\lambda$ is incident on the optical element along the optical path. A lens 3 focuses the light into the optical element 1. Emerging light is collimated by a similar lens 4 and passed through a filter 5 adapted to remove light of wavelength $\lambda$ while passing light of wavelength $\lambda/2$.

Optical element 1 is preferably a single crystal having at least one dimension of about 0.25 mm or greater, but can be substantially smaller crystals imbedded in a film of polymer or in glass. The smaller crystals can be randomly orientated or aligned with the same orientation, and are preferably aligned. For the smaller crystals, if their size is small enough to prevent light scattering, they can be dispersed in a polymeric binder and pressed, molded or shaped into an optically clear element capable of SHG. The polymeric binder should be chosen to be a nonsolvent for the MMONS. Suitable binders include polymethacrylate, poly(methyl methacrylate), polylvinyl alcohol), copolymers of methyl methacrylate and methacrylic acid, copolymers of styrene and maleic anhydride and half ester-acids of the latter, and Scotch ®-type tape. For larger crystallites, similar elements can be prepared if the binder used has an index of refraction matched to the complex, so as to prevent light scatter and remain transparent.

Figure 2:
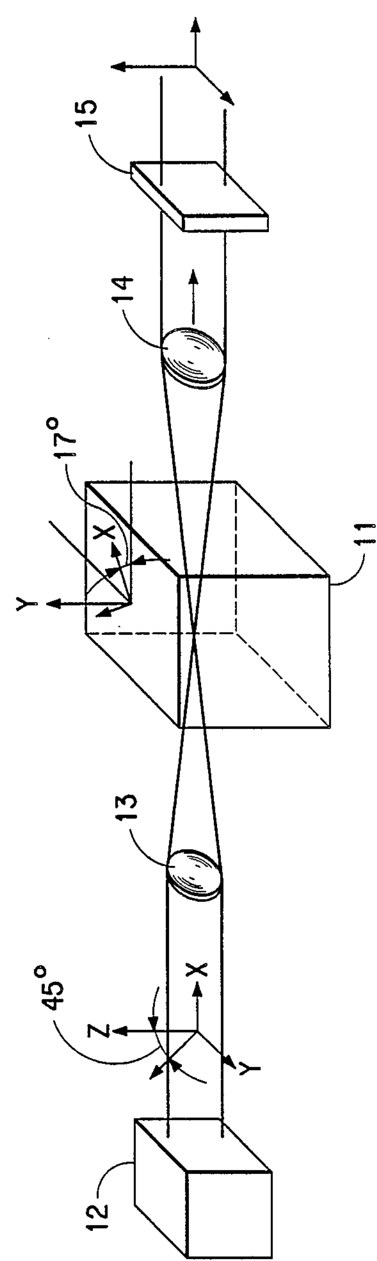
FIG. 2 illustrates a method of generating second harmonic radiation using a crystal of 3-methyl-4-methoxy-4'-nitrostilbene (MMONS).

Referring to FIG. 2, a crystal of MMONS 11 is shown oriented so that the y direction (corresponding to the b-axis of the Aba2 space group) is oriented vertically and the x-axis (corresponding to the crystallographic a axis) is oriented at 17° to the optical path through the crystal. Polarized light of wavelength 1.06μ from a Nd-YAG laser 12 is incident on the crystal along the optical path, the plane of polarization being oriented at 45° from the y direction. A lens 13 having a focal length of 15 cm focuses the light into the crystal. Light emerging from the crystal is collimated by a similar lens 14 and passed through a filter 15 adapted to remove light of wavelength 1.06μ. The second harmonic of the incident light emerges with its plane of polarization parallel to the Y direction.

The critical phase matching conditions, $$n_y(2\omega)=\frac{1}{2}\,[n_y(\omega)+n(\omega)]$$

wherein $$\frac{1}{n(\omega)^2}=\frac{\sin^2 17^\circ}{n_x^2}+\frac{\cos^2 17^\circ}{n_z^2}$$

are Satisfied by the above selection of conditions at ambient temperature.

For the above experimental arrangement and with light propagating along the x=a direction, noncritical phase matching can be accomplished at ambient temperature for light of wavelength 1.028 μ when incident light is polarized in the Y-Z plane (crystallographic b-c plane) at 45° from the Z axis; the condition being $$n_y(2\omega)=\frac{1}{2}\,[n_y(\omega)+n_z(\omega)]$$

It will be further apparent to those skilled in the art that the MMONS optical element of the invention is useful in other devices utilizing their nonlinear properties, such as sum and different frequency mixing, parametric oscillation and amplification, and the electro-optic effect. The use of crystals having nonlinear optical properties in optical devices is known in the art, as shown by U.S. Pat. Nos. 3,747,022, 3,328,723, 3,262,058 and 3,949,323.

The electro-optic modulator aspect of the invention comprises means for producing and directing a coherent beam of electromagnetic radiation into the optical element, and means to apply an electric field to the element in a direction to modify the transmission property of the beam.

Figure 3:
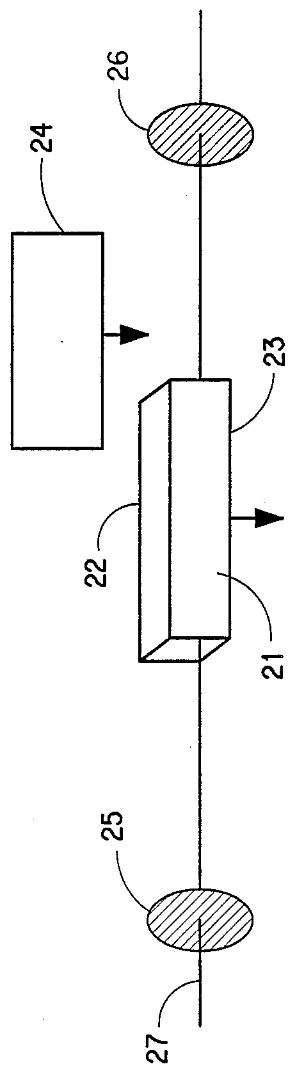
FIG. 3 is a schematic view of an electro-optic modulator of the invention.

Referring now to FIG. 3, an electro-optic modulator embodying the invention utilizes optical element 21. A pair of electrodes 22 and 23 are attached to the upper and lower surfaces of the element 21, across which a modulating electric field is applied from a conventional voltage source, 24. Optical element 21 is placed between polarizers 25 and 26. A light beam 27, such as that from a Nd-YAG laser, is polarized by polarizer 25, focused on the optical element 21, propagated through the crystal or crystals and subjected to modulation by the electric field. The modulated light beam is led out through analyzer polarizer 26. Linearly polarized light traversing element 21 is rendered elliptically polarized by action of the applied modulating voltage. Polarizer 26 renders the polarization linear again. Application of the modulating voltage alters the birefringence of element 21 and consequently the ellipticity impressed on the beam. Polarizer 26 then passes a greater or lesser fraction of the light beam as more or less of the elliptically polarized light projects onto its nonblocking polarization direction.

Figure 4:
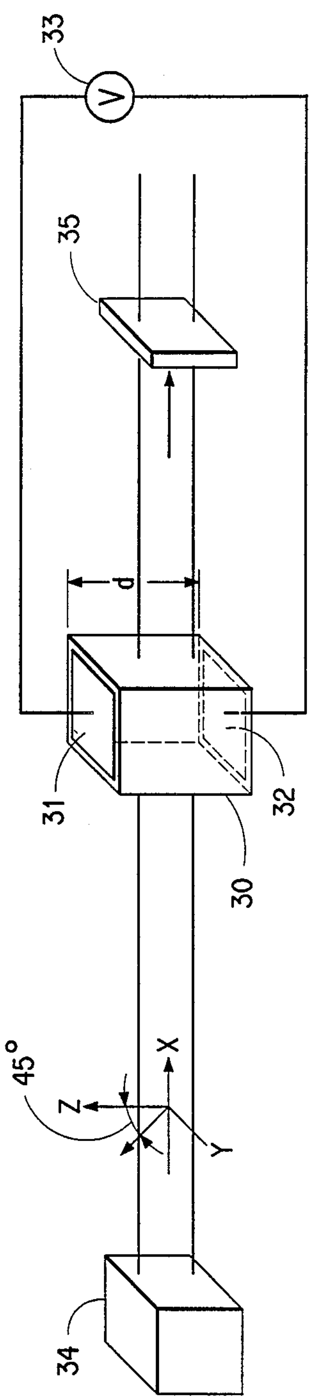
FIG. 4 illustrates a method of modulating the intensity of a beam of solarized light using a crystal of MMONS.

In FIG. 4 a crystal cube 30 of MMONS is cut with faces perpendicular to the X, Y, and Z axes. The cube is equipped with electrodes 31, 32 on the two opposing faces cut perpendicular to the Z axis. A voltage V can be applied to electrodes 31 and 32, which are spaced by a distance d, from a voltage source 33. Light from a source 34 such as a Nd-YAG laser, polarized in the yz plane is incident on the crystal 30, which is oriented with its X axis along the optical path. Light emerging from the crystal after traveling a distance L in the crystal passes through a polarizer 35.

Upon passing through a crystal, the Z component of the radiation is retarded with respect to the Y component by an amount given by $$\Gamma=\frac{2\pi L}{\lambda}(n_z-n_y)+\frac{\pi L V}{\lambda d}(n_z^3 r_{33}-n_y^3 r_{23})$$

wherein $r_{33}$ and $r_{23}$ are the linear electrooptic coefficients.

L is selected to satisfy $$\frac{2\pi L}{\lambda}(n_z-n_y)=(2m+1)\frac{\pi}{2}$$

where m in an integer or zero. With this pathlength the output beam is polarized at 90° to the input beam at zero voltage. Polarizer 35 is set to block the exit beam. Application of voltage changes Γ thereby permitting radiation to pass the polarizer 35.

The electrooptic coefficients, $r_{33}$ and $r_{23}$, were determined using a Mach-Zehnder interferometer (J. D. Bierlein and C. B. Arweiler, Appl. Phys Lett , 49, 917 [1986]) to be $r_{33}=39.9$ pm/V and $r_{23}=19.3$ pm/V.

Preparation of MMONS used in the nonlinear optical devices of this invention is given in the Examples. Generally, it has been found that the crystal growing medium affects the measured value of SHG. The solvent used for crystallizing MMONS may be polar (e.g., ethanol, ethyl acetate), non-polar (e.g., toluene) or a mixture of solvents (e.g., chloroform/ethanol). Preferably the mixture of solvents is chloroform/ethanol. In a preferred technique, a layer of ethanol is allowed to diffuse slowly into a chloroform solution of MMONS. The solubility of MMONS in the ethanol/chloroform mixture decreases as the ethanol content in the mixture increases. As the chloroform solution changes from pure chloroform to a mixture of ethanol and chloroform, a supersaturation condition is established, leading to the spontaneous nucleation of MMONS crystals, typically in the 1–2 $mm^3$ size range. Crystals in this size range can then be used to grow larger MMONS crystals by a slow cooling technique or by a solvent evaporation technique, a preferred embodiment of the latter is described in the Examples.

Crystals having a least dimension greater than 1 mm are readily obtained by the procedures outlined above and described hereinafter. The crystals have a transmission window for wavelengths ranging from about 0.51 $\mu$ to about 1.7 $\mu$ and are positive biaxially birefringent with a large difference between $n_z$ and the other two principle refractive indices, $n_x$ and $n_y$, which renders them suitable for both critical and noncritical phase matching for SHG and for other applications of nonlinear optic materials.

For MMONS the three refractive indices can be described by the Sellmeier relations $$n^2 - 1 = a_1 + \frac{a_2}{(1 - (a_3/\lambda)^2)}$$

with

| Index | $a_1$ | $a_2$ | $a_3$ ($\mu$) |
|---|---|---|---|
| $n_x$ | 0.987 | 0.314 | 0.363 |
| $n_y$ | 1.184 | 0.405 | 0.403 |
| $n_z$ | 1.507 | 1.130 | 0.421 |

For SHG critical Type I and Type II phase matching can be achieved at room temperature with this material over the range of transmission. For electromagnetic radiation propagating along the x direction and having the incident beam at 45° to the z axis, a second harmonic wave polarized along the y axis emerges which is noncritically phase matched for 1.028 $\mu$ radiation at room temperature. The temperature can be used to "tune" the above noncritical phase matching conditions to suit a particular source, e.g., a Nd-YAG laser giving a fundamental wavelength of 1.064 $\mu$.

For the mm2 point group the coefficients $d_{24}$, $d_{31}$, $d_{32}$, $d_{33}$, and $d_{15}$ of the second order polarizability tensor (expressed in conventional matrix notation with $d_{ijk}$–$d_{i\mu}$) are non-zero. Thus for SHG $$P_X(2\omega) = 2d_{15}E_X(\omega)\, E_Z(\omega)$$

$$P_Y(2\omega) = 2d_{24}E_Y(\omega)\, E_Z(\omega)$$

$$P_Z(2\omega) = d_{31}\, E_X^2(\omega) + d_{32}\, E_Y^2(\omega) + d_{33}\, E_Z^2(\omega)$$

wherein $E_k(\omega)$ is the electric field in the Kth direction, $d_{i\mu}$ is the nonlinear optical coefficient and $P_i(2\omega)$ is the induced second harmonic polarization along the $i^{th}$ direction.

The nonlinear optical coefficients $d_{33}$ and $d_{32}$ were determined by the Maker fringe technique (P. D. Maker, R. W. Terhune, M. Nisenhoff, and C. M. Savage, Phys. Rev. Letters 8, 21 1962]) to be $d_{33}=184$ pm/V and $d_{32}=41$ pm/V. The nonlinear optical coefficient $d_{24}$ was determined by the phase-matched second harmonic generation technique (F. Zernike and J. E. Midwinter, "Applied Nonlinear Optics", p. 83 (Wiley, New York, 1973) to be $d_{24}=71$ pm/V.

The invention is further illustrated by the following Examples. SHG shown in the Table was measured by the powder method of burtz et al., J. Appl. Phys., Vol. 39, 3798 (1968), using a Nd YAG laser (wavelength 1.064 $\mu$m) and urea as a reference. The polycrystalline urea powder used as a reference had an average particle size of 90 $\mu$m to 125 $\mu$m. The intensity of the second harmonic radiation generated by the sample was thus measured relative to that provided by urea.

EXAMPLE 1

Sodium ethoxide (prepared from 0.70 g of Na and 30 mL of ethanol) was added to an ice-cold mixture of diethyl p-nitrobenzylphosphonate (9.09 g, 0.033 mole) and 3-methyl-p-anisaldehyde (5.0 g, 0.033 mole) in ethanol (about 100 mL). The resulting mixture was stirred overnight. The solid product was filtered, washed with ethanol and vacuum dried to give MMONS, 3-methyl-4-methoxy-4'-nitrostilbene (4.946 g, 0.0157 mole, 47.6% yield, m.p. 109°–111° C.). Recrystallization of MMONS from chloroform/ethanol gave crystals suitable for x-ray analysis.

$^1$H nmr ($\delta$, $CD_2Cl_2$): 8.17 (d, J=8.8 Hz, 2H); 7.62 (d, J=8.8 Hz, 2H); 7.36 (overlapping d+s, 2H); 7.24 (d, J=16 Hz, 1H); 7.03 (d, J=16 Hz, 1H); 6.83 (d, J=8.2 Hz, 1H); 3.85 (s, 3H); and 2.23 (s, 3H).

SHG data for samples of MMONS recrystallized from various solvents are given in the Table.

TABLE

SHG DATA FOR 3-METHYL-4-METHOXY-4'-NITROSTILBENE

| SHG, Relative to Urea | Crystal Growing Medium |
|---|---|
| 555 | Hot ethanol |
| 727 | Hot ethyl acetate |
| 574 | Hot toluene |
| 1250 | Chloroform/ethanol |

EXAMPLE 2

Three grams of MMONS, prepared according to the procedure described in Example 1, was added to 25 ml of a chloroform/ethanol (0.8/1 by volume) mixture. After stirring at room temperature for a period of about 24 hours, 10 ml of the clear saturated solution (solubility about 50 g/l) was transferred into a crystal growth apparatus consisting of a 25 ml vial with a rubber septum and a magnetic stirring mechanism. A small 1 $mm^3$ seed crystal of MMONS was melted onto the tip of a thin (0.010 inch diameter) platinum wire which was fed through a gauge-20 hypodermic needle. The needle was introduced into the crystal growth vial through the rubber septum, and was used to control the exact location of the seed crystal in the solution. Preferential evaporation of the chloroform in the solution took place via the orifice of the needle and led to the controlled crystallization on the seed. The evaporation process was allowed to continue for 10 days and yielded a large (0.39 g, 0.3 $cm^3$) optical quality crystals of MMONS. An acute growth anisotropy was observed along the polar axis (crystallographic c-axis) in the MMONS crystal, making substantially the entire crystal available for measurements and optical device application. The crystal morphology of MMONS was rhombic with predominately {111} and {111} faces, although other faces, including the {100}, {120}, {110}, {211} and $\{21\bar{1}\}$, were also observed.

Although the invention has been described with reference to preferred embodiments, variations and modifications are included within the scope of the invention, which is defined by the claims.

I claim:

1. The nonlinear optically active compound 3-methyl-4-methoxy-4'-nitrostilbene.

2. The compound of claim 1 which is crystallized in a noncentrosymmetric space group.

3. A frequency converter comprising means for producing at least one beam of electromagnetic radiation, an optical element comprising 3-methyl-4-methoxy-4'-nitrostillbene which is crystallized in a noncentrosymmetric space group and means for directing the radiation into the optical element.

4. A method for doubling the frequency of a beam of electromagnetic radiation, comprising radiating with said beam an optical element comprising 3-methyl-4-methoxy-4'-nitrostilbene crystallized in a noncentrosymmetric space group.

5. An electro-optic modulator comprising means for producing a coherent beam of electromagnetic radiation; an optical element comprising 3-methyl-4-methoxy-4'-nitrostilbene crystallized in a noncentrosymmetric space group; and means for applying an electric field to said optical element.

6. A method for converting the frequency of a beam of electromagnetic radiation into at least one other frequency comprising irradiating a noncentrosymmetric single crystal of 3-methyl-4-methoxy-4'-nitrostilbene, the crystal having an x-axis, with at least one incident beam of radiation at a preselected frequency to produce at least one exit beam of radiation, the crystal being oriented relative to the direction of propagation of the incident beam such that the incident beam and exit beam are phase-matched.

7. The method of claim 6 wherein the crystal is irradiated by a single incident beam of radiation.

8. The method of claim 6 wherein the incident beam has a wavelength of 1.028$\mu$ and is propagated along the x-axis of the crystal.

* * * * *